US011589814B2

(12) United States Patent
Harrison et al.

(10) Patent No.: US 11,589,814 B2
(45) Date of Patent: Feb. 28, 2023

(54) SYSTEM FOR WEARABLE, LOW-COST ELECTRICAL IMPEDANCE TOMOGRAPHY FOR NON-INVASIVE GESTURE RECOGNITION

(71) Applicant: CARNEGIE MELLON UNIVERSITY, Pittsburgh, PA (US)

(72) Inventors: Christopher Harrison, Pittsburgh, PA (US); Yang Zhang, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 979 days.

(21) Appl. No.: 15/739,886

(22) PCT Filed: Jun. 27, 2016

(86) PCT No.: PCT/US2016/039656
§ 371 (c)(1),
(2) Date: Dec. 26, 2017

(87) PCT Pub. No.: WO2016/210441
PCT Pub. Date: Dec. 29, 2016

(65) Prior Publication Data
US 2018/0360379 A1    Dec. 20, 2018

Related U.S. Application Data

(60) Provisional application No. 62/231,170, filed on Jun. 26, 2015.

(51) Int. Cl.
*A61B 5/00*    (2006.01)
*A61B 5/0536*    (2021.01)
(Continued)

(52) U.S. Cl.
CPC ............ *A61B 5/681* (2013.01); *A61B 5/0536* (2013.01); *A61B 5/6824* (2013.01);
(Continued)

(58) Field of Classification Search
CPC ..... A61B 5/681; A61B 5/0536; A61B 5/6824; A61B 5/7264; A61B 2560/0209;
(Continued)

(56) References Cited

U.S. PATENT DOCUMENTS

2006/0116599 A1    6/2006  Davis
2012/0232398 A1    9/2012  Roham et al.
(Continued)

OTHER PUBLICATIONS

O.L. Silva et al., "A proposal to monitor muscle contraction through the change of electrical impedance inside a muscle," 5th IEEE RAS/EMBS International Conference on Biomedical Robotics and Biomechatronics, Sao Paulo, 2014, pp. 763-767, doi: 10.1109/BIOROB.2014.6913870. (Year: 2014).*
(Continued)

*Primary Examiner* — Alex M Valvis
*Assistant Examiner* — Chanel J Jhin
(74) *Attorney, Agent, or Firm* — Michael G. Monyok

(57) ABSTRACT

The disclosure describes a wearable, low-cost and low-power Electrical Impedance Tomography system for gesture recognition. The system measures cross-sectional bio-impedance using electrodes on wearers' skin. Using all-pairs measurements, the interior impedance distribution is recovered, which is then fed to a hand gesture classifier. This system also solves the problem of poor accuracy of gesture recognition often observed with other gesture recognition approaches.

16 Claims, 6 Drawing Sheets

(51) Int. Cl.
  *G06F 3/01* (2006.01)
  *G06F 1/16* (2006.01)

(52) U.S. Cl.
  CPC ............ *A61B 5/7264* (2013.01); *G06F 1/163* (2013.01); *G06F 3/014* (2013.01); *G06F 3/017* (2013.01); *A61B 2560/0209* (2013.01); *A61B 2562/043* (2013.01)

(58) Field of Classification Search
  CPC ... A61B 2562/043; G06F 1/163; G06F 3/014; G06F 3/017
  USPC .......................................................... 600/547
  See application file for complete search history.

(56) References Cited

U.S. PATENT DOCUMENTS

| 2012/0326911 | A1 | 12/2012 | Niwa et al. |
| 2013/0321009 | A1 | 12/2013 | Aliakseyeu |
| 2014/0094675 | A1 | 4/2014 | Luna et al. |
| 2014/0126759 | A1 | 5/2014 | Rasmussen et al. |
| 2014/0296935 | A1 | 10/2014 | Ferree et al. |

OTHER PUBLICATIONS

International Search Report and Written Opinion of the International Searching Authority for PCT Application PCT/US2016/039656 dated Sep. 30, 2016.

Cheng, J et al. "Activity recognition and nutrition monitoring in every day situations with a textile capacitive neckband." In Proceedings of the 2013 ACM conference on Pervasive and ubiquitous computing adjunct publication, pp. 155-158. ACM, 2013.

Cornelius, C. et al. "A wearable system that knows who wears it." In Proceedings of the 12th annual international conference on Mobile systems, applications, and services, pp. 55-67. ACM, 2014.

Dementyev, A. et al. "WristFlex: low-power gesture input with wrist-worn pressure sensors." In Proceedings of the 27th annual ACM symposium on User interface software and technology, pp. 161-166. ACM, 2014.

Fukui, R. et al. "Hand shape classification with a wrist contour sensor: development of a prototype device." In Proceedings of the 13th international conference on Ubiquitous computing, pp. 311-314. ACM, 2011.

Jung, P-G et al. "A wearable gesture recognition device for detecting muscular activities based on air-pressure sensors." IEEE Transactions on Industrial Informatics 11, No. 2 (2015): 485-494.

Kim, D. et al. "Digits: freehand 3D interactions anywhere using a wrist-worn gloveless sensor." In Proceedings of the 25th annual ACM symposium on User interface software and technology, pp. 167-176. ACM, 2012.

Perng, J. et al. "Acceleration sensing glove (ASG)." In Wearable Computers, 1999. Digest of Papers. The Third International Symposium on, pp. 178-180. IEEE, 1999.

Rekimoto, Jun. "Gesturewrist and gesturepad: Unobtrusive wearable interaction devices." In Wearable Computers, 2001 Proceedings Fifth International Symposium on, pp. 21-27. IEEE, 2001.

Saponas, T. et al. "Demonstrating the feasibility of using forearm electromyography for muscle-computer interfaces." In Proceedings of the SIGCHI Conference on Human Factors in Computing Systems, pp. 515-524 ACM, 2008.

Saponas, T. et al. "Enabling always-available input with muscle-computer interfaces." In Proceedings of the 22nd annual ACM symposium on User interface software and technology, pp. 167-176. ACM, 2009.

Sato, M. et al. "Touché: enhancing touch interaction on humans, screens, liquids, and everyday objects." In Proceedings of the SIGCHI Conference on Human Factors in Computing Systems, pp. 483-492 ACM, 2012.

Way, D. et al. "A usability user study concerning free-hand microgesture and wrist-worn sensors." In Wearable and mplantable Body Sensor Networks (BSN), 2014 11th International Conference on, pp. 138-142. IEEE, 2014.

Xu, C. et al. "Finger-writing with smartwatch: A case for finger and hand gesture recognition using smartwatch." In Proceedings of the 16th International Workshop on Mobile Computing Systems and Applications, pp. 9-14. ACM, 2015.

\* cited by examiner

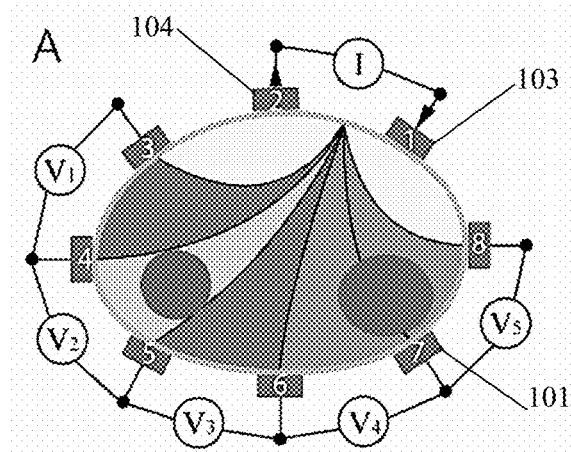 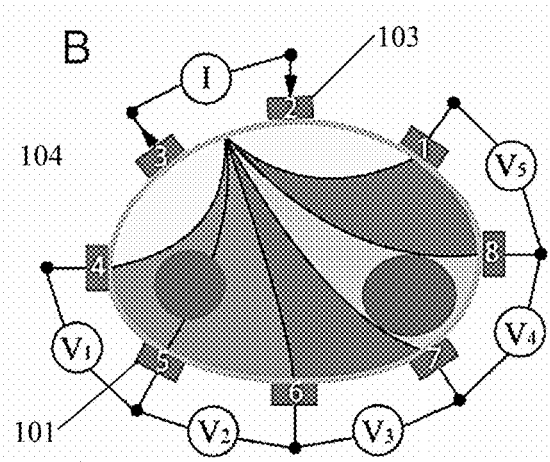
FIG. 5A   FIG. 5B
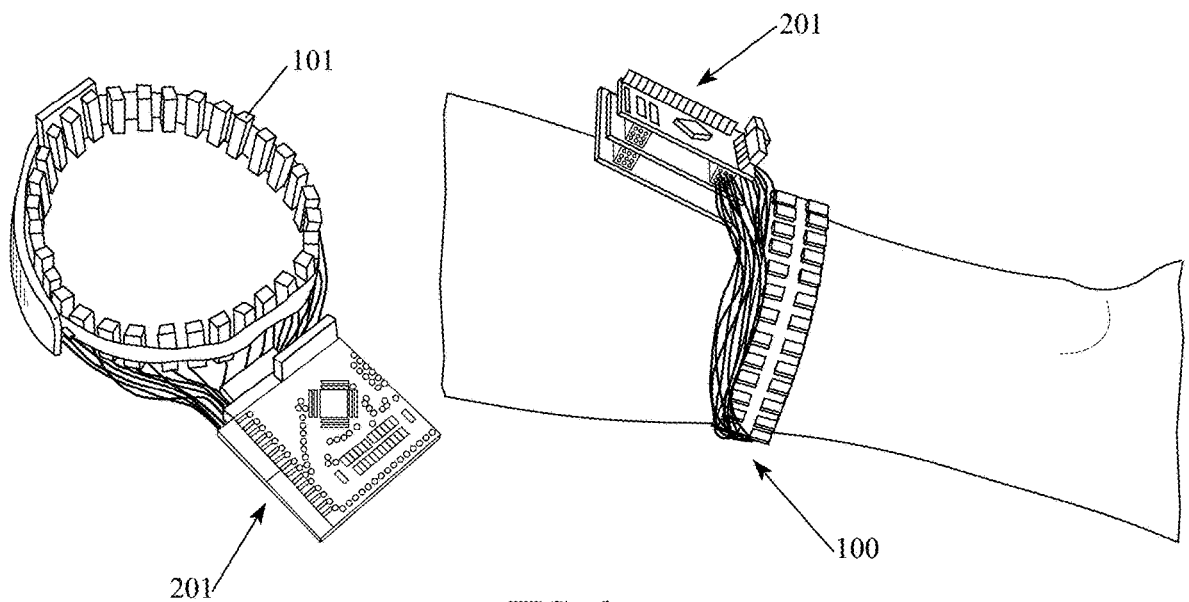
FIG. 6

SYSTEM FOR WEARABLE, LOW-COST ELECTRICAL IMPEDANCE TOMOGRAPHY FOR NON-INVASIVE GESTURE RECOGNITION

CROSS-REFERENCE TO RELATED APPLICATIONS

The present application is a 35 U.S.C. 371 US national phase application of PCT international application serial number PCT/US2016/39656, entitled "System for Wearable, Low-Cost Electrical Impedance Tomography for Non-Invasive Gesture Recognition" filed on Jun. 27, 2016, which claims priority to U.S. Provisional Application Ser. No. 62/231,170, filed Jun. 26, 2015, all incorporated by reference herein in their entirety.

STATEMENT REGARDING FEDERALLY SPONSORED RESEARCH

Not applicable.

BACKGROUND OF THE INVENTION

This invention relates generally to gesture recognition. More specifically, the invention relates to wearable devices capable of gesture recognition through the use of electrical impedance tomography.

Tomography analyzes the inner structure and composition of objects through the use of external, penetrating signals, such as electricity and radiation. Electrical Impedance Tomography (EIT) uses surface electrodes and high frequency AC signals to measure internal electrical impedance. When several electrodes are used, an internal impedance distribution be determined. Because dissimilar materials within an object will respond to signals differently, the object's cross-sectional interior structure can be reconstructed based on the variations within the impedance distribution.

Compared with other tomographic methods such as CT scans (x-rays), PET scans (gamma rays), EIT is non-invasive and relatively inexpensive. EIT is safe for long-term continuous operation (e.g., low voltage, no ionizing radiation) and is non-invasive to the wearer (rests on skin without the need for e.g., conductive gel). It has been widely applied in the medical field for the assessment of cardiac function, pulmonary hypertension, and regional lung function.

Since its introduction in the early 1980s, EIT instrumentation has continued to evolve in step with advances in electronics. However, even today, medical EIT systems continue to be relatively large and expensive, precluding integration into consumer electronics. Due to these drawbacks, the technique has not been utilized in the human-computer interaction domain, which extends interaction of computers beyond clicking and typing.

As a result, other sensing techniques have been developed for gesture recognition. One approach is to use computer vision, where 3D models of the hand are reconstructed using a wrist worn camera. Another uses a time-of-flight camera to sense small free-hand gestures. Other work has leveraged sensors on the wrist to detect dynamic hand motions such as finger rubbing and hand waving. Others have also studied arm contour changes that occur when performing different hand gestures, where the deformations are captured by sensing capacitance. While these various systems provide some level of gesture recognition, many have steep computational requirements and are fairly bulky. Computer vision systems, for example, need a line of sight to the fingers to operate, requiring the camera to be slightly elevated.

Similar to EIT systems are systems that use bio-sensing. For example, electromyography (EMG) senses the electrical signals produced by muscle activation. Another approach is bioacoustics, which measures micro-vibrations that propagate through the body upon performing hand gestures through the use of contact microphones. Drawbacks of these systems are that they do not detect a robust set of hand gestures and accuracy can be limited. In addition, some of these techniques are expensive, require calibration each time the system is worn, or require a semi-invasive gel to improve conductivity with the body.

It would therefore be advantageous to develop a low-cost, wearable system that is capable of accurately recognizing several hand gestures of a user.

BRIEF SUMMARY OF THE INVENTION

According to one embodiment of the present invention is a wearable, low-cost, and non-invasive system using Electrical Impedance Tomography (EIT) for gesture recognition. In one embodiment, the system comprises a plurality of electrodes placed on a user's arm, wrist, or other body part. The system measures the electrical characteristics of a circuit comprised of a pair of electrodes of the plurality of electrodes and an internal portion of the user's body part. Using the measurements from all electrode pair combinations, the system can recover the interior impedance distribution of a cross-section of the body part. After a series of measurements are taken, an image of the internal structure is reconstructed and the image is then transmitted to a gesture classifier. Different hand gestures will produce different impedance profiles because muscles change their cross-sectional shape and impedance distribution when flexed. As such, after training the system with different hand gestures, the classifier is able to match the reconstructed image with the different hand gestures.

By identifying hand gestures of a user, the system enables hand gestures and direct touch manipulation to work synergistically to support interactive tasks on small screens or wearable devices, such as a smartwatch, for example. Results of tests conducted with one embodiment of the present invention showed accuracies of up to 97% when worn on the wrist or arm.

BRIEF DESCRIPTION OF THE SEVERAL VIEWS OF THE DRAWINGS

FIGS. 5A-5B illustrate two projection rounds in a four-pole measurement scheme with eight electrodes.

FIG. 6 is an alternative example embodiment with electrodes placed around a user's arm.

DETAILED DESCRIPTION OF THE INVENTION

In one embodiment, the system 100 uses Electrical Impedance Tomography (EIT) to recover the inner impedance distribution of an object based on pair-wised measurements from surface electrodes 101 surrounding the object, such as a user's wrist or arm. In one embodiment, the system 100 is worn by the user and the electrodes 101 contact the skin of the user directly or, alternatively, the electrodes 101 contact the user through a thin layer of insulator (i.e. capacitive coupling).

Figure 1:
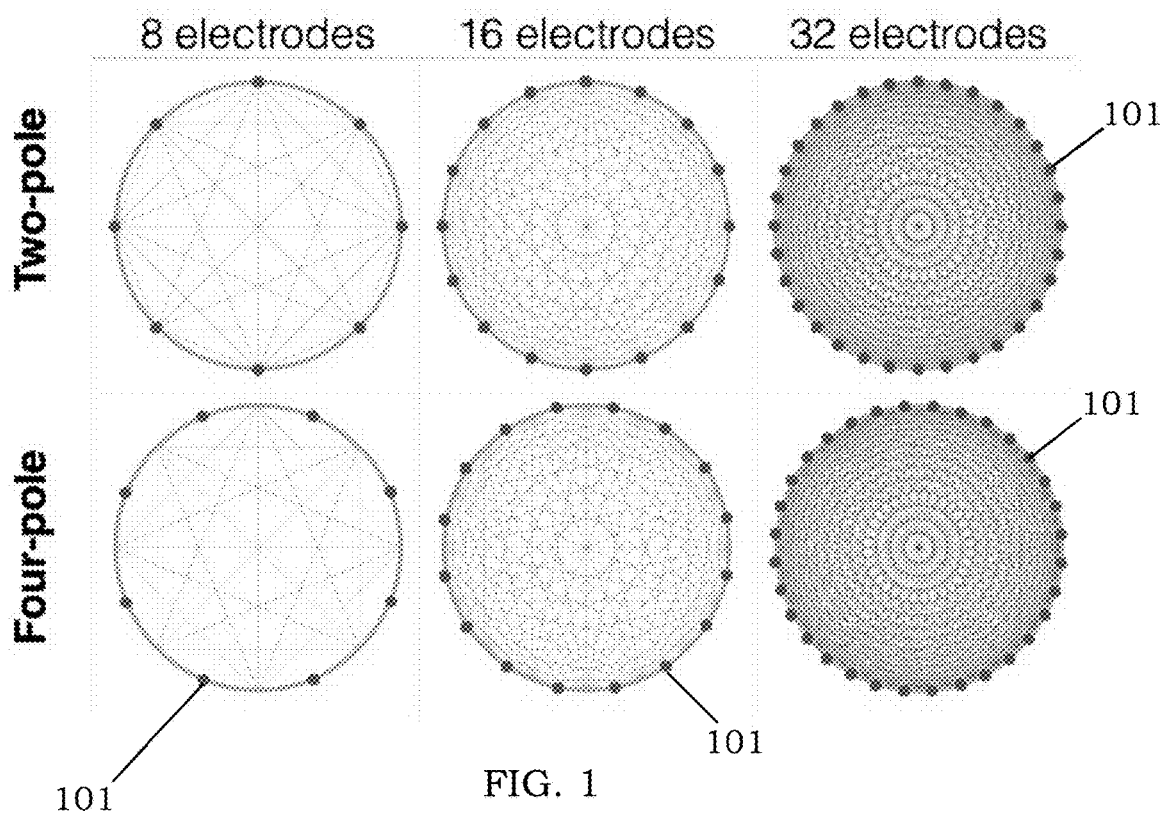
FIG. 1 is a diagram showing the various connections between paired electrodes placed around an object.

The number of electrodes 101 is a parameter that can be varied based on the intended application and the accuracy required for the particular application. For example, different embodiments of the present invention utilize 8, 16, and 32 electrodes 101. Intuitively, more electrodes 101 produce a denser mesh of sensed paths, which yields a superior reconstructed image, or cross-sectional representation of the internal structure of the object. For example, FIG. 1 illustrates the number of sensed paths, which are represented by lines, for different numbers of electrodes 101. Of note, unlike directional waves (e.g., X-rays), electric current is not confined to a plane and thus a change in impedance anywhere in the domain (i.e., not just along the path ray) will affect the measurement. Thus, increasing the number of electrodes 101 improves sensing fidelity.

Figures 2A, 2B:
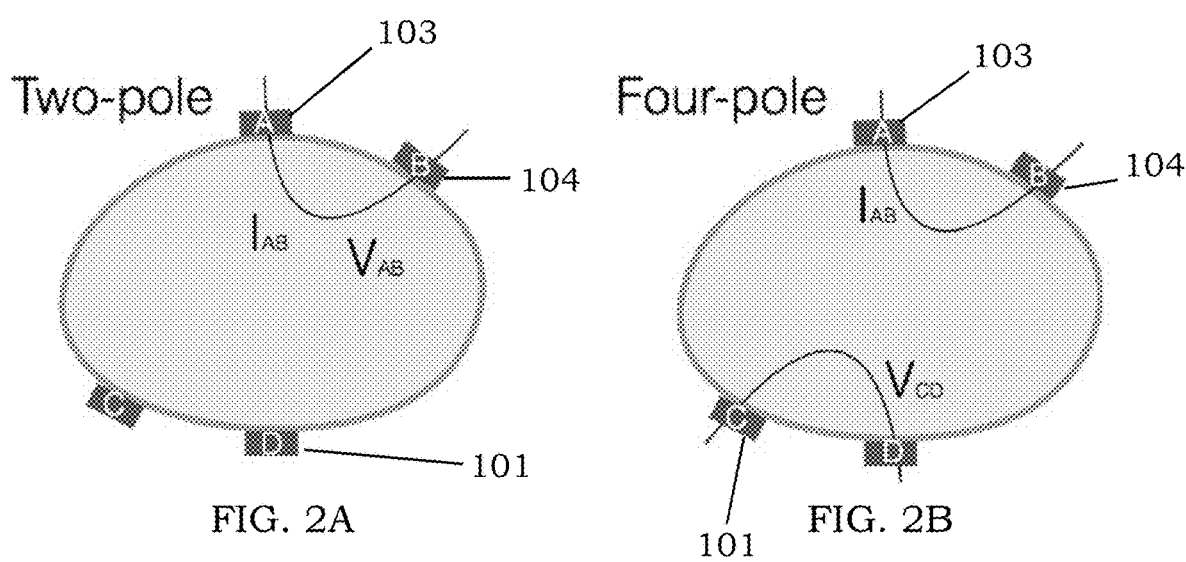
FIGS. 2A-2B are diagrams illustrating two-pole and four-pole sensing schemes.

Another parameter that affects accuracy is the type of EIT sensing, with four-pole and two-pole schemes being the most prevalent measurement strategies. FIGS. 2A and 2B illustrate the different sensing schemes between the two. With "two-pole" sensing (FIG. 2A), pairwise impedance measurements are captured from skin electrodes 101, with one transmitting electrode 103 and one receiving electrode 104 during any one single measurement. This method is known to be affected by skin impedance and so larger electrodes 101 are typically used (i.e., for greater contact area with the skin). However, this is problematic for dense electrode arrays. Nonetheless, this approach has the benefit of technical simplicity and lower costs.

Alternatively, the system 100 can use a more sophisticated "four-pole" scheme (FIG. 2B), which excites adjacent pairs of electrodes 101 with an AC signal. Impedance is measured between the transmitting electrode 103 and the receiving electrode 104. In addition, the voltage is measured between all remaining pairs of electrodes 101. This process is repeated for all electrode 101 combinations, similar to two-pole sensing. In general, four-pole sensing is less sensitive to contact conditions at the skin and provides greater impedance geometry resolution. In one embodiment, the system 100 toggles between two- and four-pole sensing schemes, as well as 8, 16 and 32 electrode configurations.

Based on user trials, the highest fidelity condition of the system 100 comprises four-pole sensing with 32 electrodes 101 and sets a new standard in EIT reconstruction on the wrist. For example, a two-pole/8 electrode system 100 supports an eleven-class gesture set at 83.3% accuracy; a four-pole/32 electrode system 100 achieves 94.3% accuracy.

Implementation

The system 100 has three main components: an array of electrodes 101 adapted to be worn by a user, a signal generator 210, and a data acquisition module 201. The signal generator 210 and data acquisition module 201 each can comprise an integrated circuit, data capture and processing board, a software-based program, or a combination of the same. In some embodiments, the signal generator 210 and data acquisition module 201 are part of the same integrated circuit.

Figure 3:
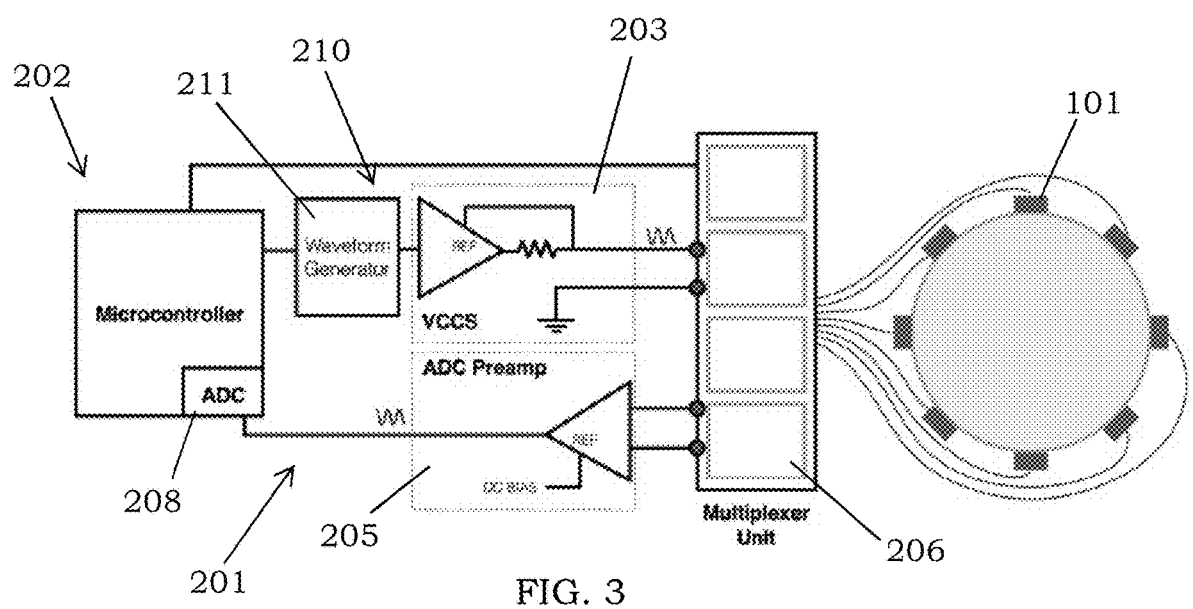
FIG. 3 is a block diagram of the system according to one embodiment.

Referring to FIG. 3, the signal generator 210 and data acquisition module 201, in one example embodiment, are built around a Cortex-M4-based Teensy 3.2 system-on-chip (SoC) 202, augmented with a voltage controlled current source (VCCS) 203, direct digital synthesis (DDS) integrated circuit, preamp 205, and an analog-to-digital converter 208. The system 101 further comprises multiplexers 206 that allow for dynamic electrode 101 selection, enabling different electrode 101 pair combinations and configurations.

Excitation Signal

To create a signal for conducting through the electrodes 101, the system utilizes a signal generator 210 comprising a waveform generator 211 in connection with the VCCS 203. In one example embodiment, the waveform generator 211 is an AD5930 DDS integrated circuit and the VCCS 203 is an AD8220-based VCCS. The waveform generator 211 is configured to output 40 KHz sinusoidal waves in one embodiment. In this example embodiment, an excitation signal of 40 kHz is used as this frequency reveals the most distinguishable signatures of gestures. However, the waveform generator 211 can produce a frequency between 0 Hz and 100 KHz with a resolution of 0.1 Hz and the frequency could differ depending on the particular application. The signal from the waveform generator 211 is then fed into the VCCS 203 to output a constant 300 µA AC current (0-6 Vpp depending on the load impedance), although the amperage and voltage of the output can vary depending on the particular application.

Multiplexing

The system 100 includes two multiplexers 206, which select any two of the electrodes 101 as a transmitting electrode 103 and a receiving electrode 104. For example, with each of the electrodes 101 labelled 1 through 8 in an eight electrode system 100, electrode number 1 will transmit the signal to electrode number 2, then subsequently transmit to electrode number 3, 4, 5, 6, 7, and 8 in sequence. In this manner, the impedance between electrode pairs 1-2, 1-3, 1-4, 1-5, 1-6, 1-7, and 1-8 is measured. Next, the multiplexer 206 designates electrode number 2 as the transmitting electrode 103 and measurements are taken for pairs 2-3, 2-4, 2-5, 2-6, 2-7, and 2-8. 2-1 does not have to be measured since that pair was already measured when electrode number 1 was the transmitter. After completing the switching for all electrodes 101, the impedance between a total of 28 non-repeating electrode pair combinations will have been measured, creating an impedance profile of the object.

In the example embodiment (during four-pole measuring), the system 100 uses two 32-to-1 multiplexers 206 (ADG732) to connect the VCCS 203 to any two electrodes 101, forming the signal-projection pair (or electrode pair combination). Another pair of multiplexers 206 connects the preamp 205 to two electrodes 101 to form the voltage-measuring pair. That is, the voltage measurement pairs are different from the current projecting pair, as shown in FIGS. 5A-5B (depicting a four-pole measuring scheme). In two-pole EIT sensing, the system 100 measures the voltage between the transmitting electrode 103 (or signal generator 210 output) and the receiving electrode 104. That is, the voltage measurement pair is the same as the signal projection pair.

Analog Sampling

In one embodiment, upon receiving the signal through the receiving electrode 104, the system 100 amplifies the signal with a preamp buffer 205. The gain value is adjusted to maintain a consistent dynamic range when switching between four-pole and two-pole measurement schemes. Additionally, a high pass filter with a 15.6 KHz cutoff frequency can be used to remove power line noise. The input signal is then biased by VDD/2 and fed to the analog-to-digital converter 208 for sampling. In one embodiment, the analog-to-digital converter 208 samples at 2 MHz with 12-bit resolution. Other sampling rates can be used, depending on the desired accuracy and system 100 requirements, among other considerations.

Data Acquisition

Once the multiplexer 206 has selected the appropriate electrodes 101, the system waits 100 µs to allow the DC bias on AC coupling capacitor to stabilize. The system then proceeds to collect 250 samples, or roughly five periods of the 40 KHz excitation signal. This oversampling helps to reduce noise. The RMS value of the signal is then computed as:

$$\text{RMS} = \sqrt{\frac{1}{N}\sum_{i}^{N}(V_i - DC_{bias})^2}$$

where N equals 250 and $DC_{bias}$ equals VDD/2=1.65. The system 100 then moves to the next measurement, reconfiguring the multiplexers 206 accordingly. After it collects all values for the current frame, it uses the RMS measurements for further analysis.

Two-Pole and Four-Pole Measurement Schemes

As previously described, when the system 100 uses a two-pole scheme, one pair of electrodes 100 is used for both signal emission and voltage measurement. In the two-pole scheme, the number of measurements is calculated as the number of unique electrode pairs:

$$N_e \times (N_e-1)/2.$$

For a two-pole system, the data acquisition module 201 computes the Discrete Fourier Transform (DFT) of the received signals and returns a real R and an imaginary I as result. The received magnitude of the DFT is given by:

$$\text{Magnitude} = \sqrt{R^2 + I^2}$$

Figure 4:
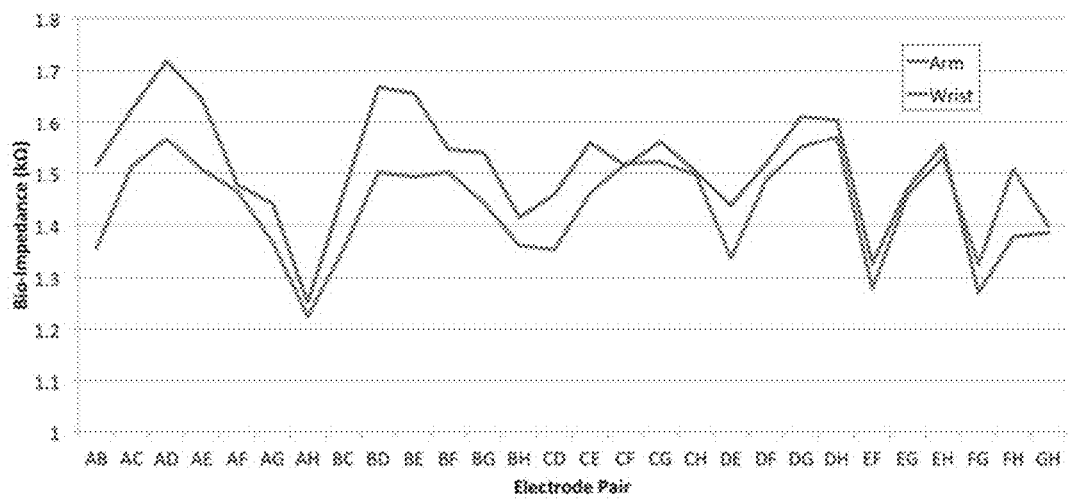
FIG. 4 is a graph of impedance measurements for different electrode pairs.

The system 100 then computes the impedance as:

$$\text{Impedance} = \frac{1}{\text{Gain Factor} \times \text{Magnitude}}$$

where the Gain Factor is computed by calibrations of each electrode pairs with 10K resisters or by placing the electrodes 101 around an homogeneous conductive object, for example, to obtain a baseline measurement of impedance between electrode pairs. FIG. 4 is an example of impedance measurements between electrode 101 pairs in an eight electrode 101 configuration.

In four-pole sensing, separate pairs are used for signal projection and voltage measurement. The Adjacent Drive method is a common projection pattern, where the signal is applied through adjacent electrodes 101 and the voltage difference is measured sequentially between all other adjacent electrode 101 pairs. FIGS. 5A-5B illustrates two rounds of data capture in an 8-electrode, four-pole scheme. During one frame of four-pole measurement, the signal-emitting pair rotates counter-clockwise through all electrodes 101, completing one cycle.

FIG. 5A illustrates the first signal projection round. The signal is emitted using E1 and E2, and the voltages differences V1, V2, V3, V4, and V5 are measured sequentially with five electrode pairs: 3-4, 4-5, 5-6, 6-7, and 7-8. In the second current projection round (FIG. 5B), the signal moves to the next pair, E2 and E3, and the voltage differences are measured sequentially with another five electrode pairs. This process is repeated sequentially until a full loop has been completed (8 rounds in this example). This is identified as one frame of data collection, which produces 8×(8−3)=40 measurements. In general, the number of four-pole measurements can be calculated as:

$$N_e \times (N_e-3).$$

Image Reconstruction

Once several impedance measurements are obtained, an image 400 of the internal structure of the object can be reconstructed. The basic goal of EIT image reconstruction is to obtain the "conductivity image" 400 of the interior of an object. The interior is discretized using a finite element method to generate a mesh, and then the conductivity at each mesh element is computed. Generally, a finer mesh produces a higher resolution output image 400.

Tomographic image reconstruction is well-studied problem in signal processing and a person having skill in the art will recognize that a number of algorithms exist. One algorithm that can be used by the system 100 is based on linear back-projection, which is commonly used for CT and PET image reconstruction. This technique assumes that the electrical current travels approximately along certain fixed equipotential lines. However, as this does not accurately capture the complete 3D movement of the electric signals, accuracy can be limited. The benefit of this method is that it is a computationally inexpensive and straightforward image reconstruction method.

Another method that can be utilized by the system 100 includes non-linear least-squares optimization to find the "best-fit" image given the data. To solve the nonlinear problem, the system 100 employs Newton-Raphson or Gauss-Newton iteration, which are computationally expensive. Thus, in an alternative embodiment, the system uses a more sophisticated single-iteration method, such as the maximum a posteriori estimator. This alternative method produces acceptable images 400 after performing significant precomputation.

In the example embodiment, the system 100 performs all image reconstruction on a computer, connected directly to the data acquisition module 201 or wirelessly, via Bluetooth for example. The image reconstruction can be performed onboard, as well. Image reconstruction algorithms known in the art can be used, such as those provided by the EIDORS MATLAB toolkit, which provides a large library of different solvers. As one example algorithm, the nodal one-step Gauss-Newton iterative solver is used to produce a maximum a posteriori (MAP) estimate of the conductivity at each node of the finite element mesh. This algorithm is parameterized by a single hyperparameter µ, which controls the smoothing of the output. In the example embodiment, the hyperparameter value is fixed at µ=0.03 for the two-pole configuration and µ=0.001 for the four pole configuration.

Gesture Classification

Gestures can be classified using features derived from either the raw impedance measurements, impedance profile created from the impedance measurements, or from the reconstructed images 400. As a result, classifying allows the conductivity profile to be associated with a gesture. Since the system 100 reconstructs images 400 sufficiently fast to be used in real-time, features can be derived purely from the reconstructed images 400 and use a support vector machine (SVM) provided by the Weka ToolKit, for example, for classification (SMO; polynomial kernel with default parameters). In some situations, image reconstruction can introduce noise, which obscures the features derived from the image 400. As such, in an alternative embodiment, the features used in classification are obtained directly from the impedance measurements or impedance profile.

User Study and Results 10 participants (3 female), all right handed, with a mean age of 24, were part of a user study to assess an example implementation. As all of the participants were right handed, the system 100 was worn on the left forearm, the conventional location for wearing a watch.

Gesture Sets

Figure 7:
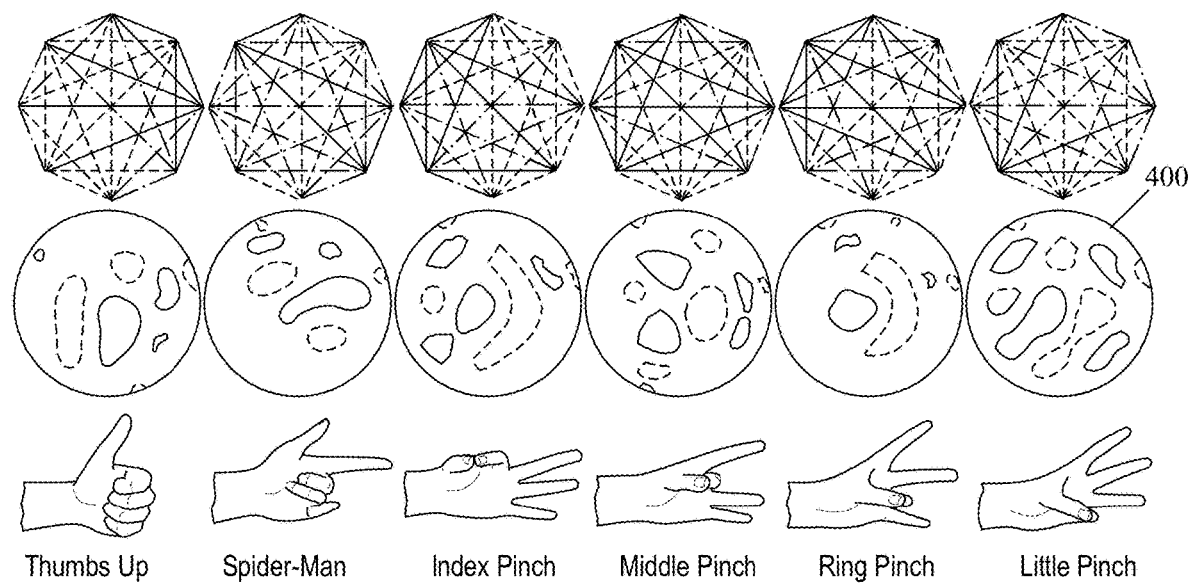
FIG. 7 is an example of different gestures.

The gesture set included a widely used thumb-to-finger pinch gesture set: Index Pinch, Middle Pinch, Ring Pinch, and Little Pinch (examples of several gestures illustrated in FIG. 7). A hand gesture set was also created, designed around coarse motions of the hand. This gesture set included Fist, Stretch, Right, Left, Thumbs Up, Spider-Man and Index Pinch. Included also was a Relax gesture in both sets as the neutral state, bringing the total number of gestures in pinch and hand sets to 5 and 8 respectively.

Procedure

After a brief introduction, participants were fitted with the wrist- and arm-bands. Of note, unlike most electromyography (EMG) systems, this approach does not require any conductive gel or other special preparation of the skin. Once comfortable, participants were asked to perform one gesture at a time. Gestures were requested visually on a laptop screen in a random order. Participants were asked to hold the gesture until a beep was emitted from the laptop; this period lasted approximately one second, during which time 10 data points were recorded. Participants were not provided with any feedback during data collection to prevent them from adjusting their hands to adapt to a classification result. A single round of data collection was complete once all gestures had been requested. In total, 10 rounds of data were collected. This procedure resulted in 11,000 data points (10 participants×11 gestures×10 data points×10 rounds). In a second round, participants followed exactly the same process as described above, except that gestures were only requested once (i.e., one round).

The data was analyzed to determine the accuracy of the system and how much training data was needed to initialize the classifiers, and to assess stability of the data, both across users and time.

Within-User Accuracy

Because users have different bodies, most bio-sensing systems require per-user classifiers (e.g., electromyography, bioacoustics). Using data collected during phrase one, from a single user at a time, the classifier was trained on nine rounds of data, testing on a tenth. This procedure ensures the data points adjacent in time (which will naturally tend to be more similar) were either in the test set or train set, but not both.

Figure 8:
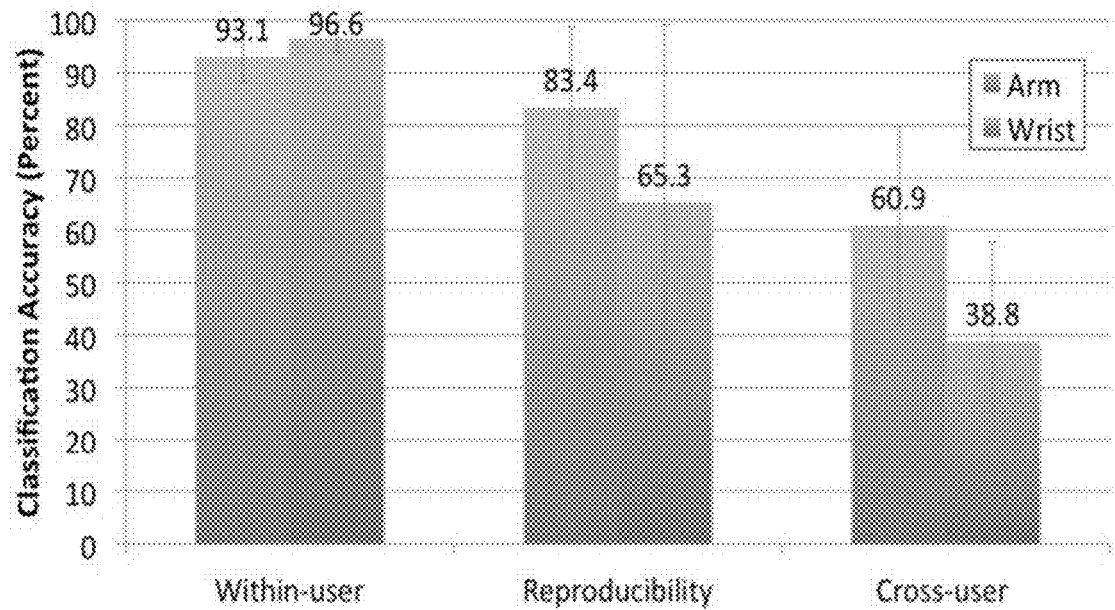
FIG. 8 shows a plot of the accuracy of the system, according to one embodiment, for a hand gesture set.

For the hand gesture set (FIG. 8), the wrist location achieves a mean accuracy of 96.6% (SD=2.8%). Meanwhile, the arm location achieves a mean accuracy of 93.1% (SD=4.7%). A major source of error is the confusion between first and Thumbs Up, contributing 28% of the mis-classifications.

Figure 9:
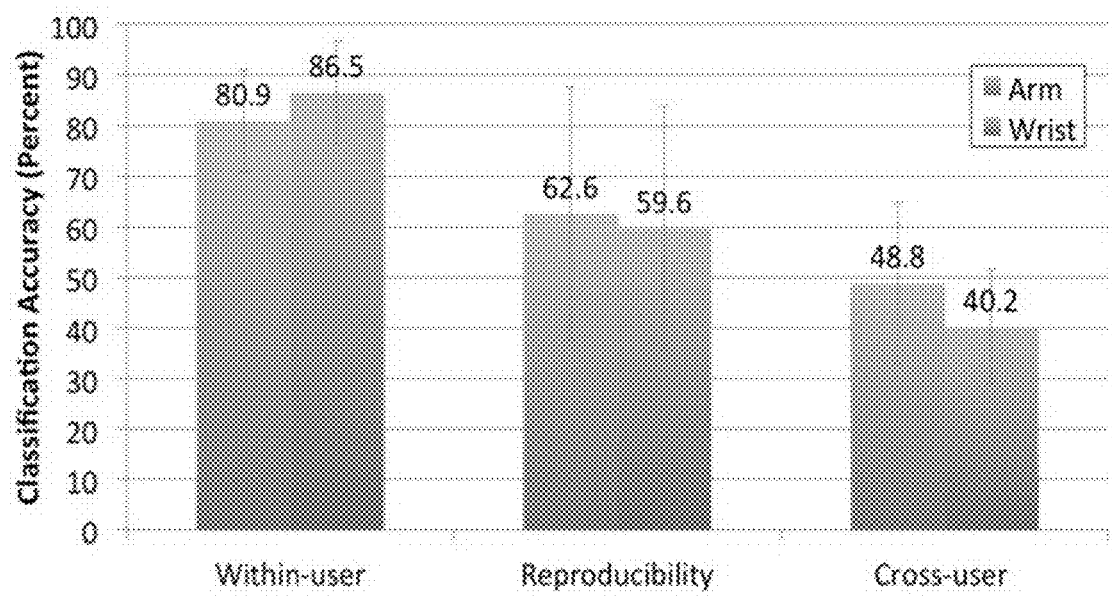
FIG. 9 shows a plot of the accuracy of the system, according to one embodiment, for a pinch gesture set.

For the pinch gesture set (FIG. 9), the accuracy in the wrist location is 86.5% (SD=10.1%). The most confused gestures are Ring Pinch and Little Pinch, contributing 27% of the misclassifications. The arm location achieves an accuracy of 80.9% (SD=10.2%). In this case, Index Pinch and Ring Pinch confusion contributes 14% of the misclassified instances.

Volume of Training Data

Figure 10:
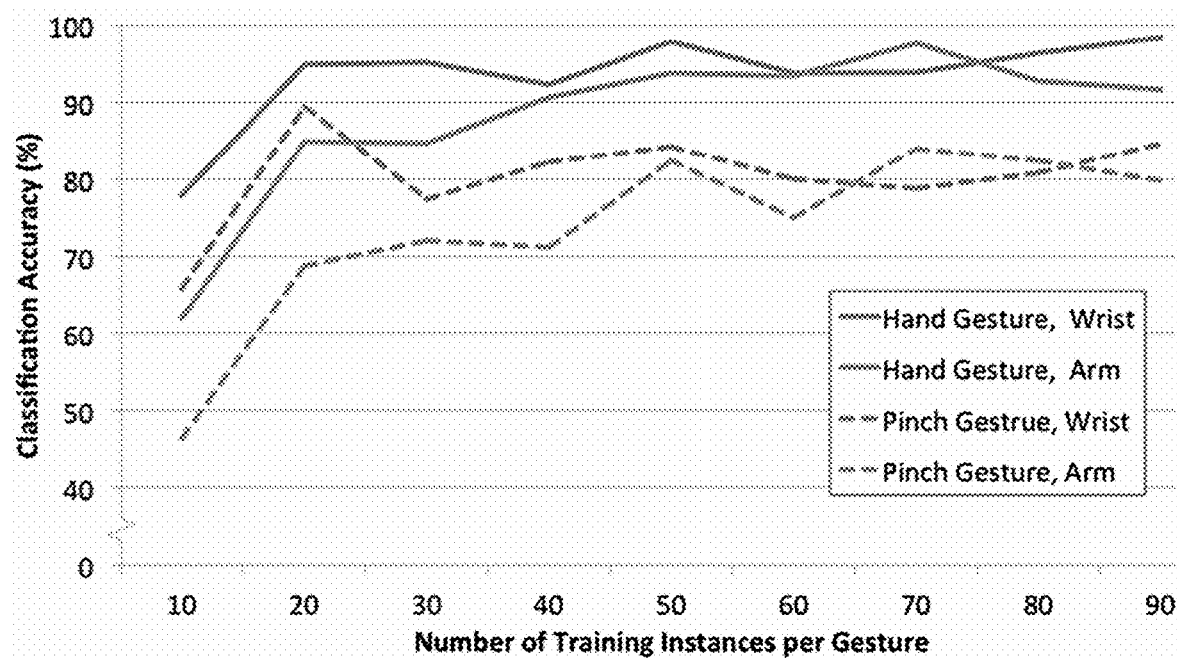
FIG. 10 is a graph showing accuracy as a function of the volume of training.

To better understand how much training data is needed before classifiers are sufficiently robust, an experiment varying the size of the training set was run (phase one data only). Specifically, the SVM was trained on round 1 data, testing on round 2. Then, trained on rounds 1 and 2, and tested on round 3, and on so up to rounds 1 though 9 being used for training and tested on round 10. The results of this analysis are shown in FIG. 10. In general, accuracy increases quickly, and largely plateaus by around 50 training instances.

Smartwatch Integration

Figure 11:
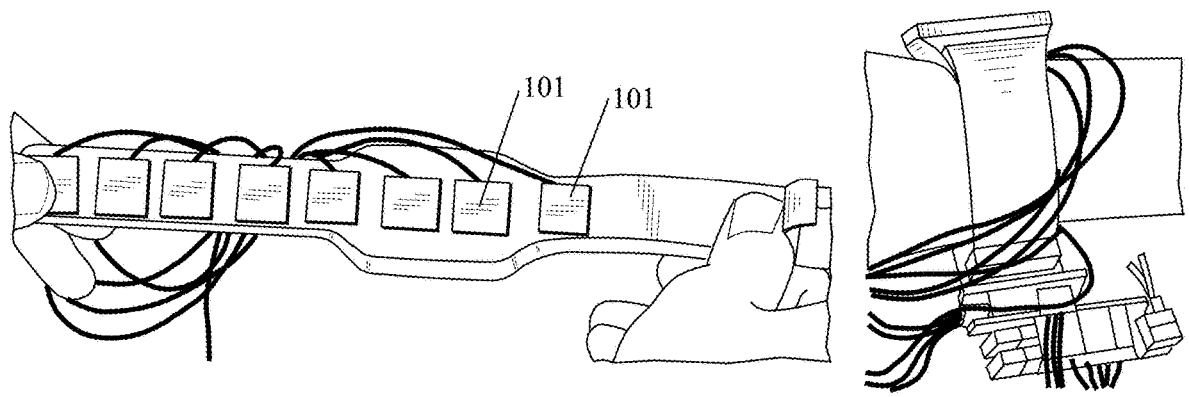
FIG. 11 is an example embodiment incorporated into a smartwatch.

In one example embodiment, the wrist strap of a Samsung Gear Smartwatch was instrumented with eight electrodes 101 (FIG. 11). The data acquisition module 201 and signal generator 210 were attached to the underside of the watch. The data acquisition module 201 transmits data to a laptop over Bluetooth, which performs classification and controls the smartwatch interface over a web socket. Additional implementations would have fully integrated capabilities within smartwatches and wearable devices.

A simple interaction sequence was created, utilizing three hand gestures. In one non-limiting example, a user can navigate through a series of messages with Left and Right gestures. If desired, a message can be opened with a first gesture and go back to the list with a Stretch gesture, exposing additional on-screen options. If a phone call pops up, it can be dismissed with a Left gesture, or expanded with a first gesture.

FIG. 6 is another example of the system 100 incorporated in to a wearable device. In this example, a leather wristband is provided with 32 evenly spaced stainless steel electrodes 101. Each electrode 101 measures 3.4×15.3 mm. The average human forearm diameter is roughly 190 mm in circumference, suggesting an upper-bound electrode width of ~6 mm in a 32-electrode configuration. The wristband is secured to the user with a Velcro strap. Further shown in FIG. 6 is data acquisition module 201.

While the disclosure has been described in detail and with reference to specific embodiments thereof, it will be apparent to one skilled in the art that various changes and modification can be made therein without departing from the spirit and scope of the embodiments. Thus, it is intended that the present disclosure cover the modifications and variations of this disclosure provided they come within the scope of the appended claims and their equivalents.

What is claimed is:

1. A system for recognizing gestures of a user, comprising:
    a plurality of electrodes adapted to be in contact with a body part of the user;
    a signal generator for generating a signal, wherein the signal generator is connected to a transmitting electrode of the plurality of electrodes;
    a data acquisition module for receiving the signal conducted through an electrical circuit comprising the transmitting electrode, an internal portion of the user's body part, and a receiving electrode of the plurality of electrodes,
wherein the data acquisition module determines an impedance of the electrical circuit based on the received signal,
wherein the data acquisition module generates an impedance profile of a cross-section of an interior of the body part based on a plurality of impedance measurements from additional electrical circuits formed from the plurality of electrodes; and
a classifier that identifies a gesture associated with a set of features derived from the impedance profile.

2. The system of claim 1, further comprising:
a multiplexer coupled to the plurality of electrodes,
wherein the multiplexer selects one electrode of the plurality of electrodes as the transmitting electrode and a different electrode as the receiving electrode.

3. The system of claim 1, wherein the signal generator comprises:
a waveform generator,
wherein the waveform generator is configured to output a sinusoidal wave having a frequency between about 0 Hz and 100 KHz; and
a voltage controlled current source connected to the waveform generator.

4. The system of claim 3, wherein the frequency is about 40 KHz.

5. The system of claim 1, wherein the data acquisition module comprises:
an analog-to-digital converter that receives an amplified signal from the preamp, wherein the analog-to-digital converter samples the amplified signal.

6. The system of claim 5, wherein the analog-to-digital converter samples the amplified signal at a rate of 2 MHz.

7. The system of claim 1, further comprising:
a multiplexer connected to a first electrode and a second electrode of the plurality of electrodes,
wherein the first electrode and the second electrode are not the same as the transmitting electrode or the receiving electrode,
wherein the data acquisition module measures a voltage between the first electrode and the second electrode.

8. The system of claim 7, wherein the first electrode and the second electrode are adjacent.

9. The system of claim 1, wherein the plurality of impedance measurements are from a plurality of non-repeating electrode pairs selected from the plurality of electrodes.

10. The system of claim 1, wherein the set of features is derived from a reconstructed image created in part from the impedance profile.

11. The system of claim 1:
wherein the body part is an arm or wrist; and
wherein the gesture is a hand gesture.

12. A method of recognizing a hand gesture of a user, comprising:
providing a plurality of electrodes capable of being worn around the user's arm or wrist in contact with skin of the user;
generating a signal;
conducting the signal through a circuit comprising a first electrode pair combination and an internal portion of the user's arm or wrist;
measuring an impedance of the circuit;
conducting the signal through additional circuits comprised of non-repeating electrode pairs;
measuring an impedance of the additional circuits;
generating an impedance profile of a cross-section of an interior of the user's arm or wrist based on the impedance of the circuit and the impedance of the additional circuits;
deriving a set of features based on the impedance profile; and
associating the set of features with a hand gesture using a classifier.

13. The method of claim 12, further comprising:
reconstructing an image based on the impedance of the circuit and the impedance of the additional circuits, wherein the set of features are derived from the image.

14. The method of claim 12, wherein the circuit further comprises:
a first electrode of the plurality of electrodes;
the internal portion of the user's arm or wrist; and
a second electrode of the plurality of electrodes.

15. The method of claim 12, further comprising:
measuring a voltage between additional electrode pair combinations not including the first electrode pair combination,
wherein the additional electrode pair combinations comprise adjacent electrodes of the plurality of electrodes.

16. The method of claim 12, wherein the electrical characteristic is impedance.

* * * * *